United States Patent
Gazda et al.

(10) Patent No.: US 8,741,637 B2
(45) Date of Patent: Jun. 3, 2014

(54) METHOD FOR ISOLATING A CHEMOTHERAPEUTIC AGENT RESISTANT CANCER CELL WITH STEM CELL PROPERTIES

(75) Inventors: Lawrence Gazda, Xenia, OH (US); Barry Smith, New York, NY (US)

(73) Assignee: The Rogosin Institute, Inc., New York, NY (US)

( * ) Notice: Subject to any disclaimer, the term of this patent is extended or adjusted under 35 U.S.C. 154(b) by 0 days.

(21) Appl. No.: 13/701,705

(22) PCT Filed: Nov. 22, 2011

(86) PCT No.: PCT/US2011/061812
§ 371 (c)(1),
(2), (4) Date: Jun. 10, 2013

(87) PCT Pub. No.: WO2012/071394
PCT Pub. Date: May 31, 2012

(65) Prior Publication Data
US 2013/0244248 A1    Sep. 19, 2013

Related U.S. Application Data

(60) Provisional application No. 61/458,391, filed on Nov. 23, 2010, provisional application No. 61/458,390, filed on Nov. 23, 2010.

(51) Int. Cl.
*C12N 5/07* (2010.01)
*C12N 5/09* (2010.01)
*C12N 5/095* (2010.01)
*C12N 11/10* (2006.01)

(52) U.S. Cl.
USPC ........... 435/325; 435/178; 435/373; 435/374; 435/382

(58) Field of Classification Search
None
See application file for complete search history.

(56) References Cited

FOREIGN PATENT DOCUMENTS

WO    WO2010/119001    * 10/2010

OTHER PUBLICATIONS

Liu et al (Molecular Cancer, 2006, vol. 5, No. 67, pp. 1-12).*

* cited by examiner

*Primary Examiner* — Karen Canella
(74) *Attorney, Agent, or Firm* — Abelman, Frayne & Schwab

(57) ABSTRACT

The invention relates to the use of encapsulates of cancer cells, in agarose coated, agarose containing beads, for isolating chemotherapeutic resistant cells which have at least one stem cell property, such as expression of OCT4. The cells thus isolated are also a feature of the invention, as is a method for screening for potential therapeutic agents.

9 Claims, No Drawings

METHOD FOR ISOLATING A CHEMOTHERAPEUTIC AGENT RESISTANT CANCER CELL WITH STEM CELL PROPERTIES

RELATED APPLICATIONS

This application is a §371 of PCT/US2011/061812 filed Nov. 22, 2011, and claims priority of provisional patent applications 61/458,390 and 61/458,391, both filed on Nov. 23, 2010, and incorporated by reference in their entirety.

FIELD OF THE INVENTION

This invention relates to methods for isolating cancer stem cells, and the cancer stem cells thus isolated. It also relates to methods for screening compounds of interest to determine if they have potential efficacy as anti-tumor agents.

BACKGROUND AND PRIOR ART

The majority of deaths from cancer following chemotherapy and remission result from recurrence of the original treated tumor or tumors. This appears to be somewhat counterintuitive, as known cancer therapies sometimes, but do not always, eliminate tumors to the point where a patient may be declared "cured."

A theory that has been advanced to explain the recurrence of tumors, as well as tumor growth per se, is the "cancer stem cell" or "CSC" theory. In brief, this theory posits that a rare population of cancer cells which possess some characteristics of stem cells undergo asymmetric division which in turn leads to replacement stem cells, and to more lineage restricted populations of tumor amplifying cells. These "new" cells proliferate rapidly, and make up the majority of the tumor, in contrast to the stem cells, which are slow-cycling, quiescent, and are resistant to therapies which target rapidly dividing cells. The result of this is that while the majority of cells in a tumor are susceptible to one or more of these targeted therapies, the small population of stem cell-like, chemo-resistant cancer cells, are not destroyed, and the cycle discussed supra repeats itself.

Clearly, there is a need to identify these stem cell-like cancer cells, as well as a need to quantify their presence in tumors of a particular subject or patient. Also, while the field of oncology recognizes a number of chemotherapies for cancer "one size does not fit all," and a need remains for developing targeted therapies, as well as a more general method for identifying potentially useful anti-tumor drugs.

U.S. Pat. Nos. 5,888,497; 6,303,151; 6,808,705; 6,818,230; 7,041,504; and 7,297,331, all of which are incorporated by reference in their entirety, describe methods for encapsulating cancer cells in agarose beads, which are in turn coated with agarose. The type of agarose may vary, as shown in the context of other cell types (islets), as per, e.g., published application 2007/0071732, also incorporated by reference in its entirety.

Work on these encapsulates of cancer cells has led to the observation that populations of cells develop which might possess properties paralleling stem cells. It was thus of interest to determine if the materials described in these references could be used to isolate chemotherapy resistant cancer cells, which also possess stem cell-like properties. In so doing, it was also learned that these encapsulates could be used to screen compounds of interest to determine if the compound is efficacious against cancers.

How these and other aspects of the invention are achieved will be seen in the disclosure which follows.

DETAILED DESCRIPTION OF PREFERRED EMBODIMENTS

Example 1

Agarose coated, agarose beads containing RENCA cells were prepared in accordance with Smith, et al., *Canc Res.*, 71(3): 716-724 (2011); and Smith et al., *Canc. Res.* 71(3): 725-735 (2011), the disclosures of which are incorporated by reference. The resulting beads were cultured in medium for 12 weeks.

Samples of beads were then exposed to a single, known anti-cancer drug, at one of three varying concentrations. The exposure involved incubation of the beads in the presence of the drug for a period of time based upon the known, half life of the drug.

Following incubation, the beads were washed, twice, and transferred to naïve culture media. Controls were also prepared, which included untreated beads, as well as beads exposed to whatever vehicle was used to solubilize the drug.

Histological examination of the beads was undertaken one week following exposure to the drug. In some cases, there was no change, while in others, the drug resulted in complete loss of cell viability and in others, and there was an intermediate effect. The results follow:

| Agent | Treatment Time | Dose | Effect |
|---|---|---|---|
| Cisplatin | 1 hr | 60 ng/ml | − |
| | | 600 ng/ml | − |
| | | 6000 ng/ml | − |
| Carboplatin | 5 days | 25 µg/ml | +/− |
| | | 250 µg/ml | + |
| | | 2500 µg/ml | + |
| Methotrexate | 1 day | 0.45 µg/ml | − |
| | | 4.5 µg/ml | − |
| | | 45 µg/ml | − |
| Doxorubicin | 2 days | 5 µg/ml | + |
| | | 50 µg/ml | + |
| | | 100 µg/ml | + |
| Vinorelbine | 2 days | 0.1 µg/ml | − |
| | | 1 µg/ml | +/− |
| | | 10 µg/ml | +/− |
| Docetaxel | 1 day | 0.5 µg/ml | +/− |
| | | 5 µg/ml | +/− |
| | | 50 µg/ml | +/− |
| Paclitaxel | 1 day | 0.35 µg/ml | − |
| | | 3.5 µg/ml | +/− |
| | | 35 µg/ml | +/− |

Example 2

Treatment with Docetaxel and Paclitaxel did not destroy all of the cells within the encapsulated tumor colonies, and thus the beads that had been treated with these drugs were selected for further study. Beads treated with Caboplatin at a low concentration, or Vinorelbine, at an intermediate concentration, could have been used as well.

The Paclitaxel and Docetaxel treated beads were cultured, under standard conditions, as were control beads which had been exposed to DMSO, which was the vehicle for delivery of the two drugs. The culture period was 18 weeks.

The encapsulated cells in DMSO treated beads exhibited normal morphology, which is elliptical tumor colonies, consisting of a rim of cells, 1-2 cells thick, surrounding internal debris. In contrast, beads which had been treated with 3.5 µg/ml of Paclitaxel showed a loss of cells for 6 weeks, with a return to the pre-treatment number of cells by week 18. The beads treated with Docetaxel (5 µg/ml) displayed a consistent pattern of only 1-2 cells per colony, at 6 weeks post-treatment. Approximately 10% of the beads developed 1 or 2 large colonies, at week 18.

In order to quantify the cell loss, representative beads from the DMSO control, Paclitaxel and Docetaxel groups were sectioned and stained, using standard methods, in order to permit counting of cell nuclei. Results were normalized to the DMSO treated beads.

In the case of treatment with Paclitaxel, there was an initial loss over weeks 1-3, of about 25% of cells per colony. The majority of colonies did contain viable cells. Cell numbers had increased after 18 weeks to be equivalent to the control DMSO beads. In the case of docetaxel treated beads, these lost viable cells very rapidly, such that only 1-2 viable cells were present in the colonies 6 weeks after treatment. At week 18, about 10% of the beads had developed 1 or 2 large colonies of cells, thus indicating that rare, Docetaxel resistant RENCA cells can form new colonies within the beads.

Example 3

Recent evidence suggests that OCT4 ("octamer binding transcription factor 4"), a marker for embryonic stem cells, can be used in conjunction with other transcription factors to induce adult cells to a pluripotent, stem cell like. See, e.g., Park et al., Nature 451 (7475): 141-146 (2008). Additional markers characteristic of stem cells may be found in, e.g, International Stem Cell Initiative, et al, Nat. Biotechnol 25(7):803-16 (2007), incorporated by reference herein.

Experiments were carried out to determine if the cells which remained in the Docetaxel treated cells, six weeks post-treatment, exhibited this marker.

The cells were stained with DAPI, to identify living cells, while standard immunochemical procedures were used to stain for OCT4, using a rabbit, polyclonal antibody to OCT4, and a goat, anti-IgG antibody labeled with a Fluor 488 conjugate.

The results indicated that the living cells expressed OCT4. The expression, taken with the resistance to Docetaxel, suggest the remaining cells are cancer stem cells.

Example 4

A requisite of cancer stem cells is the ability to form colonies of cancer cells. To determine if the cells described supra could do so, the colonies were dislodged from beads, and surviving cells were harvested, via mechanical disruption, 5-6 weeks after removal, and colonies were minced with forceps in RPMI 1640 plus 10% newborn calf serum. The suspension was then put through a 40 µm cell strainer, so as to minimize any agarose debris, and pelleted via centrifugation. Cell pellets were resuspended, in naïve culture medium and cultured either in vitro (200 cells/ml, in RPMI 1640 supplemented with 10% newborn calf serum), or cultured in vivo. To elaborate, 200 cells were mixed with a drop of blood from a recipient mouse, thus forming a clot, which was then implanted under a kidney capsule of the mouse from which blood was taken. The mice were then observed for growth of tumors. The development of a tumor after in vivo transplantation of purified stem cells is considered the art-recognized "gold standard" for identifying cancer stem cells.

The RENCA cells grown in vitro were much larger than normal RENCA cells which were grown in monolayer, and they were not observed to undergo cell growth for about 16 weeks. It 16-17 weeks post-culture, cells formed plaques and begun proliferating upon weekly passage, and growing as a monolayer in culture. But two weeks after the start of monolayer growth, these cells had growth rates which were comparable to normal RENCA cells, and appeared as normal RENCA monolayer cells, with equivalent size and morphology.

Of the ten mice which received implants, one developed a tumor under the capsule, and died 98 days post-induction. It had also developed a lung metastasis.

The results indicate that these cells may thus be considered cancer stem cells.

The foregoing examples set forth various aspects of the invention, which include a method for isolating cancer cells which are resistant to chemotherapeutic agents, such as Docetaxel, and which possess one or more properties of stem cells, such as expression of OCT4. Other properties of stem cells are well known to the art and are not repeated here. The method involves encapsulating a sample of cancer cells in an agarose containing bead which is then coated with agarose, culturing the resulting bead to grow the cancer cells contained therein, contacting the bead with a chemotherapeutic agent, and determining which of said remaining cells express OCT4, either in situ or by removal therefrom.

This method can be used, e.g., to develop a prognosis for a subject suffering from cancer, because as noted supra, cells of the type described herein are responsible for recurrence of cancer in subjects. Essentially, a high percentage of said cells indicates a poorer prognosis for a patient than would be the case for a patient who exhibits few, or no such cells in the encapsulated sample.

Any chemotherapeutic agent may be used in the method of the invention, as can any type of cancer. The skilled artisan will be aware of many other known therapeutic agents for cancer therapy. Similarly, it will be recognized from, e.g., the references cited supra, that various cancers and agaroses may be used, in addition to those described herein. Also, the beads of the invention may include materials such as collagen, or other materials compatible with agarose. The cancer cells are preferably mammalian cells, and most preferably, human cells.

The fact that the isolated cells are resistant to the known chemotherapeutic agents reported herein does not, however, mean that they are chemoresistant "per se." The agents tested herein, as indicated, are drugs which are useful, generally, in the destruction of rapidly proliferating cells. There are other therapies available for cells of the type represented by the cells remaining in the agarose coated, agarose beads, which will be known to the skilled artisan. While not reported herein, such drugs may be tested against these stem cell-like, chemotherapeutically resistant OCT4 expressing cells, and a therapeutic regime may be developed where, e.g., a subject receives, as a first course of therapy, a standard anti-cancer agent, followed by an agent directed to the type of cells isolated and described herein. Such cells are isolated cancer cells which are resistant to chemotherapeutic agents, such as Docetaxel, and which express OCT4. In this aspect of the invention, the substance of interest may be tested against the stem-cell like cancer cells remaining after the contact with the first agent, or one may encapsulate a separate sample of stem cell like cancer cells and proceed in the same fashion.

The skilled artisan will also note that the invention relates to a method for determining if a compound of interest has efficacy as an anti-cancer agent. As will be seen, the method involves contacting a compound of interest to an agarose coated, agarose bead, which contains a sample of cancer cells, for a chosen period of time and at a chosen concentration, and determining if said compound destroys a percentage of cells greater than a control. In such cases, the compound may be considered to be therapeutically useful, as well as useful in non-therapeutic contexts, such as use in destroying cancer cells in a mixed cell population, or in eliminating non-stem cell cancer cells from a mix of cells. Also contemplated are "cocktails" of more than one potentially useful therapeutic agent, or combinations of known therapeutic agents with test compounds, to determine if combination therapy or application in non-therapeutic contexts, is appropriate.

Other features of the invention will be clear to the skilled artisan and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claims:

1. A method for isolating a chemotherapeutic agent resistant cancer cell with stem cell properties, comprising:
   (i) encapsulating a sample of cancer cells in an agarose coated, agarose containing bead;
   (ii) contacting said bead with at least one anti-cancer chemotherapeutic agent for a time sufficient to kill at least a portion of said cancer cells;
   (iii) removing any surviving cells from said bead;
   (iv) assaying said surviving cell for at least one stem cell property, and
   (v) isolating any cells which exhibit said stem cell property from any cells which do not.

2. The method of claim 1, wherein said stem cell property is expression of OCT4.

3. The method of claim 1, wherein said chemotherapeutic agent is Docetaxel.

4. The method of claim 1, wherein said cancer cells are mammalian cells.

5. The method of claim 4, wherein said mammalian cells are human cells.

6. A method for determining if a substance of interest has anti-cancer efficacy, comprising (i) contacting said substance to a sample of cancer cells encapsulated in an agarose containing, agarose coated bead, (ii) determining percentage of said cancer cells killed by said substance, and (iii) comparing said percentage to percentage of said cancer cells encapsulated in an agarose containing, agarose coated bead killed by a control agent, wherein a higher percentage killed by said substance is indicative of anti-cancer efficacy for said substance.

7. The method of claim 6, wherein said cancer cells are mammalian cancer cells.

8. The method of claim 7, wherein said mammalian cancer cells are human cancer cells.

9. A method for determining if a substance of interest has anti-cancer stem cell activity comprising encapsulating cancer stem cells in an agarose containing, agarose coated bead, contacting said bead with said substance, and comparing number of remaining cells to a cancer stem cell containing bead not contacted with said substance, where a difference there between indicates said substance has anti-cancer stem cell activity.

* * * * *